United States Patent [19]

Iwasaki et al.

[11] Patent Number: 4,771,072
[45] Date of Patent: Sep. 13, 1988

[54] ALKOXYNAPHTHALENE DERIVATIVES

[75] Inventors: Tameo Iwasaki, Nishinomiya; Kohki Takashima, Tokyo, both of Japan

[73] Assignee: Tanabe Seiyaku Co., Ltd., Osaka, Japan

[21] Appl. No.: 814,805

[22] Filed: Dec. 30, 1985

[30] Foreign Application Priority Data

Jan. 10, 1985 [JP] Japan .................................. 60-3090

[51] Int. Cl.$^4$ ..................... A61K 31/235; C07C 63/38
[52] U.S. Cl. ...................................... 514/533; 560/56;
549/433; 549/299; 549/298
[58] Field of Search .......................... 560/56; 514/533

[56] References Cited

PUBLICATIONS

Iwao et al., C.A., 101, 192026m (1984)–Abstract of Chem. Lett., 1984 (7), 1263–6.
Brian A. Keay et al., "Hydroxyacetats, Phthalans, and Isobenzofurans Therefrom", Canadian Journal of Chemistry, vol. 61, pp. 1987–1995 (1983).
S. Osmund De Silva et al., "A Regiocontrolled Synthesis of Some Arylnaphthalide Lignans", The Journal of the Chemical Society, Chemical Communications, pp. 995–997 (1980).
G. Traverso, Chemical Abstracts, vol. 53, 20025i–20027i (1959) and Gazzetta Chimica Italiana, vol. 88, 517–522 (1958).
Heinz P. Plaumann et al., "Potential Isobenzofurans: Their Use in the Synthesis of Naturally Occurring 1-A-rylnaphthalide Lignans", The Journal of the Chemical Society, Chemical Communications, 354–355 (1980).
A. G. Gonzalez et al., "Synthesis of Two Arylnaphthalene Lignans", Tetrahedron, vol. 34, 1011–1013 (1978).
Shibnath Ghosal et al., "Two New Aryl Naphthalide Lignans from Polygala Chinensis", Phytochemistry, vol. 13, 1933–1936 (1974).

Primary Examiner—Nicky Chan
Attorney, Agent, or Firm—Browdy and Neimark

[57] ABSTRACT

Naphthalene derivative of the formula:

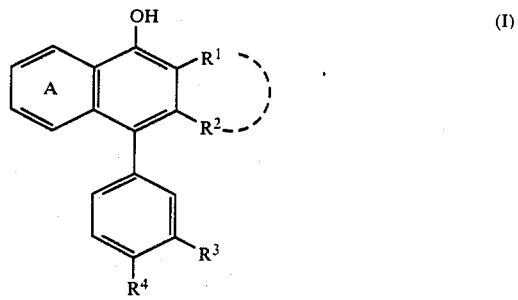

wherein
$R^1$ is hydrogen atom or a lower alkoxycarbonyl and
$R^2$ is a lower alkoxycarbonyl, or $R^1$ and $R^2$ are combined together to form a group of the formula:

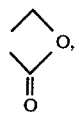

, each of $R^3$ and $R^4$ is a lower alkoxy, or one of $R^3$ and $R^4$ is hydrogen atom and the other is a lower alkoxy, and
Ring A is a substituted or unsubstituted benzene ring, and a pharmaceutically acceptable salt thereof are disclosed. Said naphthalene derivative (I) and its salt have excellent hypolipidemic activity and are useful for treatment or prophylaxis of hyperlipidemia and/or arteriosclerosis.

7 Claims, No Drawings

ALKOXYNAPHTHALENE DERIVATIVES

This invention relates to naphthalene derivatives useful as hypolipidemic agents.

Hyperlipidemia such as hypercholesterolemia has been known to be a major risk factor for arteriosclerosis including atherosclerosis, and drugs such as clofibrate [chemical name: 2-(4-chlorophenoxy)-2-methylpropanoic acid ethyl ester], probucol [chemical name: 4,4'-[(1-methylethylidene)bis(thio)]bis[2,6-bis(1,1-dimethylethyl)phenol]] and cholestyramine resin have been used as hypolipidemic agents.

It is known that cholesterol in blood serum exists in various forms such as very-low-density lipoprotein (VLDL) cholesterol, low-density lipoprotein (LDL) cholesterol and high-density lipoprotein (HDL) cholesterol. In this connection, it is also known that HDL has therapeutic or prophylactic effect for arteriosclerosis because of its preventing effect on deposition of cholesterol on the arterial wall, while VLDL and LDL induce the deposition of cholesterol and are causative of arteroisclerosis [Annals of Internal Medicine, vol. 90, page 85–91 (1979)].

Therefore, in the field of therapy or prophylaxis of arteriosclerosis, it has been desired to develop a hypolipidemic agent which can decrease the serum total cholesterol level and at the same time can increase the serum HDL-cholesterol level.

On the other hand, Journal of the Chemical Society (Chemical Communications), page 354 (1980), discloses 1-(3,4-dimethoxyphenyl)-2,3-bis(methoxycarbonyl)-4-hydroxy-6,7-methylenedioxynaphthalene and 1-(3,4-dimethoxyphenyl)-3-hydroxymethyl-4-hydroxy-6,7-methylenedioxy-2-naphthoic acid lactone. Further, Chemical Abstracts, vol. 53, 20025i (1959) discloses 1-(3,4-dimethoxyphenyl)-3-hydroxymethyl-4-hydroxy-6,7-dimethoxy-2-naphthoic acid lactone and 1-(3,4-dimethoxyphenyl)-2-ethoxycarbonyl-4-hydroxy-6,7-dimethoxynaphthalene. However, no therapeutic effect of these compounds has been known up to now.

As a result of various investigations, we have now found that a naphthalene derivative of the formula:

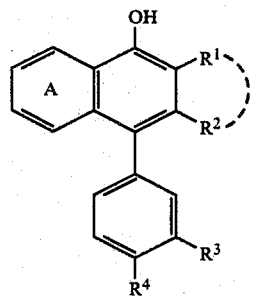
(I)

wherein
R$^1$ is hydrogen atom or a lower alkoxycarbonyl and R$^2$ is a lower alkoxycarbonyl, or R$^1$ and R$^2$ are combined together to form a group of the formula

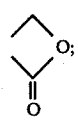

each of R$^3$ and R$^4$ is a lower alkoxy, or one of R$^3$ and R$^4$ is hydrogen atom and the other is a lower alkoxy; and Ring A is a substituted or unsubstituted benzene ring; and a pharmaceutically acceptable salt thereof are useful as a hypolipidemic agent.

Thus, an object of the present invention is to provide a naphthalene derivative (I) which is useful for therapeutic treatment or prophylaxis of hyperlipidemia and/or arteriosclerosis. Another object is to provide a novel pharmaceutical composition for use as a hypolipidemic agent, which comprises the naphthalene derivative (I) as the therapeutically active ingredient. The other object is to provide a novel naphthalene derivative useful as a hypolipidemic agent. And still other object is to provide processes for preparing said novel naphthalene derivative.

The naphthalene derivative (I) or a pharmaceutically acceptable salt thereof shows a potent hypolipidemic activity and is particularly characterized in that it can increase the serum HDL-cholesterol level while decreasing the serum total cholesterol level. For example, when the effect of a test compound (dose: 20 mg% in diet) on the serum total cholesterol level and the serum HDL-cholesterol level was examined by feeding rats with a diet supplimented with cholesterol and sodium cholate, 1-(3,4-dimethoxyphenyl)-2,3-bis(methoxycarbonyl)-4-hydroxy-6,7,8-trimethoxynaphthalene of the present invention showed 52% decrease in serum total cholesterol level and 86% increase in the serum HDL-cholesterol level.

Moreover, the naphthalene derivative (I) and a pharmaceutically acceptable salt thereof are low in toxicity and substantially free from undesirable side effects such as hepatic dysfunction. For example, when 1-(3,4-dimethoxyphenyl)-2,3-bis(methoxycarbonyl)-4-hydroxy-6,7,8-trimethoxynaphthalene was administered orally to mice at a dose of 1000 mg/kg, no mice died even 5 days after the oral administration.

Representative examples of the naphthalene derivative of the present invention include those of the formula (I) in which R$^1$ is hydrogen atom or a lower alkoxycarbonyl (e.g., methoxycarbonyl, ethoxycarbonyl, propoxycarbonyl, butoxycarbonyl) and R$^2$ is a lower alkoxycarbonyl) e.g., methoxycarbonyl, ethoxycarbonyl, propoxycarbonyl, butoxycarbonyl); or R$^1$ and R$^2$ are combined together to form a group of the formula:

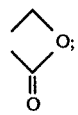

each of R$^3$ and R$^4$ is a lower alkoxy (e.g., methoxy, ethoxy, propoxy, isopropoxy, butoxy), or one of R$^3$ and R$^4$ is hydrogen atom and the other is a lower alkoxy (e.g., methoxy, ethoxy, propoxy, isopropoxy, butoxy); and Ring A is an unsubstituted benzene ring, a benzene ring having a substituent of a lower alkylenedioxy (e.g., methylenedioxy, ethylenedioxy) or a benzene ring having one to 3 substituent(s) selected from the group consisting of a lower alkyl (e.g., methyl, ethyl, propyl, isopropyl, butyl), a lower alkoxy (e.g., methoxy, ethoxy, propoxy, isopropoxy, butoxy), a phenyl-lower alkoxy (e.g., benzyloxy, phenethyloxy), hydroxy and halogen atom (e.g., fluorine atom, chlorine atom, bromine atom, iodine atom).

Among these derivatives, preferred examples include those of the formula (I) in which $R^1$ is hydrogen atom or a lower alkoxycarbonyl and $R^2$ is a lower alkoxycarbonyl, or $R^1$ and $R^2$ are combined together to form a group of the formula:

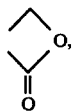

each of $R^3$ and $R^4$ is a lower alkoxy, or one of $R^3$ and $R^4$ is hydrogen atom and the other is a lower alkoxy, and Ring A is a benzene ring of the formula:

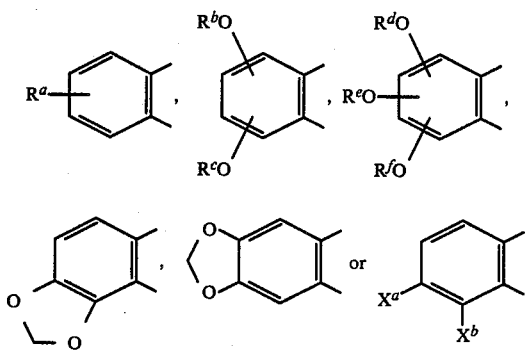

wherein $R^a$ is hydrogen atom, a lower alkyl (e.g., methyl, ethyl, propyl, isopropyl, butyl) or a lower alkoxy (e.g., methoxy, ethoxy, propoxy, isopropoxy, butoxy), $R^b$ is a lower alkyl (e.g., methyl, ethyl, propyl, isopropyl, butyl), $R^c$ is hydrogen atom, a lower alkyl (e.g., methyl, ethyl, propyl, isopropyl, butyl) or a phenyl-lower alkyl (e.g., benzyl, phenethyl), each of $R^d$, $R^e$ and $R^f$ is a lower alkyl (e.g., methyl, ethyl, propyl, isopropyl, butyl) and each of $X^a$ and $X^b$ is halogen atom (e.g., fluorine atom, chlorine atom, bromine atom, iodine atom).

Another preferred examples of the naphthalene derivative (I) include 1-(3,4-dimethoxyphenyl)-2,3-bis(methoxycarbonyl)-4-hydroxy-6,7,8-trimethoxynaphthalene, 1-(3,4-dimethoxyphenyl)-2-methoxycarbonyl-3-ethoxycarbonyl-4-hydroxy-6,7,8-trimethoxynaphthalene, 1-(3,4-dimethoxyphenyl)-2-ethoxycarbonyl-3-methoxycarbonyl-4-hydroxy-6,7,8-trimethoxynaphthalene, 1-(3,4-dimethoxyphenyl)-2,3-bis(ethoxycarbonyl)-4-hydroxy-6,7,8-trimethoxynaphthalene, 1-(3,4-dimethoxyphenyl)-2,3-bis(methoxycarbonyl)-4-hydroxy-6,7-methylenedioxynaphthalene, 1-(3,4-diethoxyphenyl)-2,3-bis(methoxycarbonyl)-4-hydroxy-6,7-methylenedioxynaphthalene, 1-(3,4-dimethoxyphenyl)-3-hydroxymethyl-4-hydroxy-6,7-methylenedioxy-2-naphthoic acid lactone, 1-(3,4-diethoxyphenyl)-3-hydroxymethyl-4-hydroxy-6,7-methylenedioxy-2-naphthoic acid lactone, 1-(3,4-dimethoxyphenyl)-3-hydroxymethyl-4-hydroxy-7,8-dichloro-2-naphthoic acid lactone, 1-(3,4-dimethoxyphenyl)-3-hydroxymethyl-4-hydroxy-7-methyl-2-naphthoic acid lactone, 1-(3,4-dimethoxyphenyl)-3-hydroxymethyl-4-hydroxy-7,8-methylenedioxy-2-naphthoic acid lactone, and the like.

The naphthalene derivative (I) may be used for the purpose of the present invention either in free form or in the form of a pharmaceutically acceptable salt. Examples of the pharmaceutically acceptable salt of the naphthalene derivative (I) include alkali metal salts (e.g., sodium salt, potassium salt), alkaline earth metal salts (e.g., calcium salt), quarternary ammonium salts (e.g., tetramethylammonium salt, tetraethylammonium salt) and so forth.

The daily dose of the naphthalene derivative (I) or a pharmaceutically acceptable salt thereof may vary over a wide range depending on the severity of the diseases; the ages, weight and condition of patient and the like, but the preferred daily dose may be usually in the range of 1.5 to 35 mg, especially 5 to 25 mg, per kg of body weight.

The naphthalene derivative (I) or a pharmaceutically acceptable salt thereof may be administered either orally or parenterally to warm-blooded animals including human beings, while it is generally preferred to administer it through oral route. The naphthalene derivative (I) or a salt thereof may be used in the form of pharmaceutical composition in admixture with a pharmaceutically acceptable adjuvant or carrier therefor. For example, the pharmaceutical composition for oral administration may be in a solid dosage form such as tablets, pills, powders, capsules or granules; and it may contain a pharmaceutically acceptable adjuvant or carrier such as calcium carbonate, calcium phosphate, corn starch, potato starch, sugar, lactose, talcum, magnesium stearate and the like. Said pharmaceutical composition in a solid form may further contain binders, diluents, disintegrants, wetting agents and so forth. Alternatively, the pharmaceutical composition for oral administration may be in a liquid dosage form such as aqueous or oily suspensions, solutions, syrup, elixirs and the like. Suitable adjuvants for such liquid dosage form may include liquid vehicles, suspending agents, surfactants, non-liquid vehicles and so forth. On the other hand, the pharmaceutical composition for parenteral administration may be in the form of injections or suppositories. The injections may be either a solution or a suspension, which may contain a pharmaceutically acceptable carrier such as essential oil (e.g., peanut oil, corn oil) or aprotic solvent (e.g., polyethyleneglycol, polypropyleneglycol, lanolin, coconut oil).

As mentioned hereinbefore, the naphthalene derivative (I) and a pharmaceutically acceptable salt thereof have a potent hypolipidemic activity. Especially, the naphthalene derivative (I) and a salt thereof are characterized in that they can decrease serum total cholesterol level and at the same time can increase the serum HDL-cholesterol level in blood. Therefore, the naphthalene derivative (I) and a salt thereof are useful for the treatment or prophylaxis of hyperlipidemia (e.g., hypercholesterolemia) or arteriosclerosis (e.g., atherosclerosis, Mönkeberg's sclerosis, arteriolosclerosis) in warm-blooded animals including human beings.

Among the naphthalene derivative (I) of the present invention, a compound of the following formula (I-a) is a novel compound.

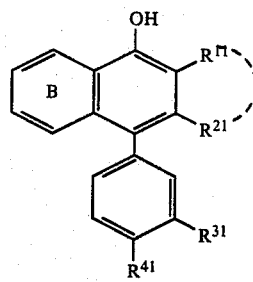

wherein

R$^{11}$ is hydrogen atom or a lower alkoxycarbonyl and R$^{21}$ is a lower alkoxycarbonyl, or R$^{11}$ and R$^{21}$ are combined together to form a group of the formula:

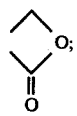

each of R$^{31}$ and R$^{41}$ is a lower alkoxy, or one of R$^{31}$ and R$^{41}$ is hydrogen atom and the other is a lower alkoxy; and Ring B is a substituted or unsubstituted benzene ring, with the provisos that (a) if both of R$^{11}$ and R$^{21}$ are methoxycarbonyl and Ring B is a benzene ring of the formula:

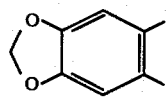

or (b) if R$^{11}$ is hydrogen atom, R$^{21}$ is ethoxycarbonyl and Ring B is a benzene ring of the formula:

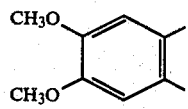

or (c) if R$^{11}$ and R$^{21}$ are combined together to form a group of the formula:

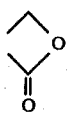

and Ring B is a benzene ring of the formula:

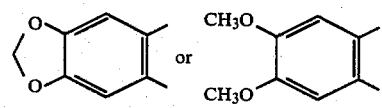

each of R$^{31}$ and R$^{41}$ is a lower alkoxy of at least 2 carbon atoms, or one of R$^{31}$ and R$^{41}$ is hydrogen atom and the other is a lower alkoxy.

Representative examples of the above-mentioned Ring B include an unsubstituted benzene ring, a benzene ring having a substituent of a lower alkylenedioxy and a benzene ring having one to 3 substituent(s) selected from the group consisting of a lower alkyl, a lower alkoxy, a phenyl-lower alkoxy, hydroxy and halogen atom.

Preferred examples of the compound (I-a) include those of the formula (I-a) in which (A) each of R$^{11}$ and R$^{21}$ is a lower alkoxycarbonyl, and (a) each of R$^{31}$ and R$^{41}$ is a lower alkoxy, or one of R$^{31}$ and R$^{41}$ is hydrogen atom and the other is a lower alkoxy, and Ring B is an unsubstituted benzene ring, a benzene ring of the formula:

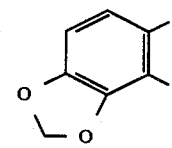

or a benzene ring having one to 3 substituent(s) selected from the group consisting of a lower alkyl, a lower alkoxy, a phenyl-lower alkoxy, hydroxy and halogen atom; or (b) each of R$^{31}$ and R$^{41}$ is a lower alkoxy of at least 2 carbon atoms, or one of R$^{31}$ and R$^{41}$ is hydrogen atom and the other is a lower alkoxy, and Ring B is a benzene ring of the formula:

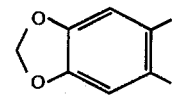

or (B) R$^{11}$ is hydrogen atom, R$^{21}$ is a lower alkoxycarbonyl, and (a) each of R$^{31}$ and R$^{41}$ is a lower alkoxy, or one of R$^{31}$ and R$^{41}$ is hydrogen atom and the other is a lower alkoxy, and Ring B is an unsubstituted benzene ring, a benzene ring having a substituent of a lower alkylenedioxy, a benzene ring having one or 3 substituent(s) of a lower alkoxy, a benzene ring having one to 3 substituent(s) selected from the group consisting of a lower alkyl and halogen atom, or a benzene ring of the formula:

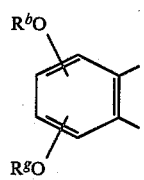

wherein R$^g$ is hydrogen atom or a phenyl-lower alkyl, and R$^b$ is the same as defined above; or (b) each of R$^{31}$ and R$^{41}$ is a lower alkoxy of at least 2 carbon atoms, or one of R$^{31}$ and R$^{41}$ is hydrogen atom and the other is a lower alkoxy, and Ring B is a benzene ring having 2 substituents of a lower alkoxy; or (C) R$^{11}$ and R$^{21}$ are combined together to form a group of the formula:

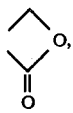

and (a) each of $R^{31}$ and $R^{41}$ is a lower alkoxy, or one of $R^{31}$ and $R^{41}$ is hydrogen atom and the other is a lower alkoxy, and Ring B is an unsubstituted benzene ring, a benzene ring having one or 3 substituent(s) of a lower alkoxy, a benzene ring having one to 3 substituent(s) selected from the group consisting of a lower alkyl and halogen atom, or a benzene ring of the formula:

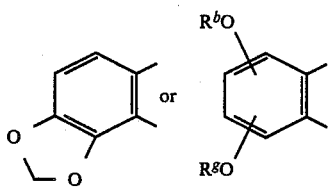

wherein $R^b$ and $R^g$ are the same as defined above; or (b) each of $R^{31}$ and $R^{41}$ is a lower alkoxy of at least 2 carbon atoms, or one of $R^{31}$ and $R^{41}$ is hydrogen atom and the other is a lower alkoxy, and Ring B is a benzene ring of the formula:

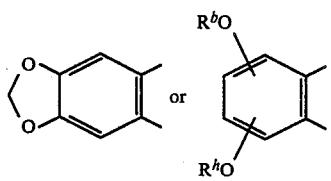

wherein $R^h$ is a lower alkyl and $R^b$ is the same as defined above.

Another preferred examples of the compound (I-a) include those of the formula (I-a) in which (A) each of $R^{11}$ and $R^{21}$ is a lower alkoxycarbonyl, and (a) each of $R^{31}$ and $R^{41}$ is a lower alkoxy, or one of $R^{31}$ and $R^{41}$ is hydrogen atom and the other is a lower alkoxy, and Ring B is a benzene ring of the formula:

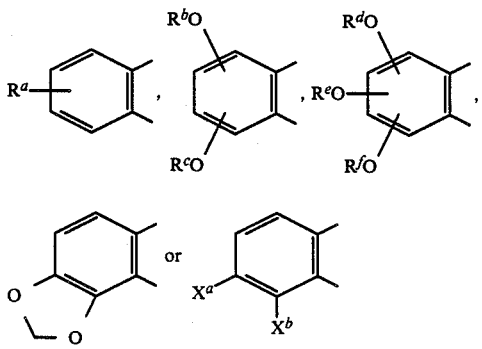

wherein $R^a$, $R^b$, $R^c$, $R^d$, $R^e$, $R^f$, $X^a$ and $X^b$ are the same as defined above; or (b) each of $R^{31}$ and $R^{41}$ is a lower alkoxy of at least 2 carbon atoms, or one of $R^{31}$ and $R^{41}$ is hydrogen atom and the other is a lower alkoxy, and Ring B is a benzene ring of the formula:

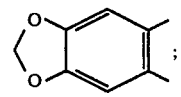

or (B) $R^{11}$ and $R^{21}$ are combined together to form a group of the formula:

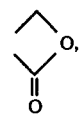

and (a) each of $R^{31}$ and $R^{41}$ is a lower alkoxy, or one of $R^{31}$ and $R^{41}$ is hydrogen atom and the other is a lower alkoxy, and Ring B is a benzene ring of the formula:

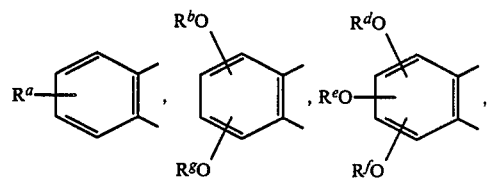

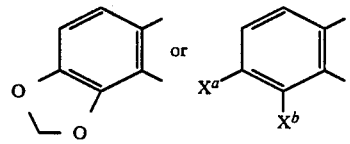

wherein $R^a$, $R^b$, $R^d$, $R^e$, $R^f$, $R^g$, $X^a$ and $X^b$ are the same as defined above; or (b) each of $R^{31}$ and $R^{41}$ is a lower alkoxy of at least 2 carbon atoms, or one of $R^{31}$ and $R^{41}$ is hydrogen atom and the other is a lower alkoxy, and Ring B is a benzene ring of the formula:

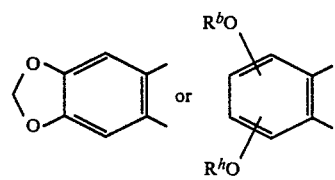

wherein $R^b$ and $R^h$ are the same as defined above.

Still another preferred examples include those of the formula (I-a) in which each of $R^{11}$ and $R^{21}$ is a lower alkoxycarbonyl, or $R^{11}$ and $R^{21}$ are combined together to form a group of the formula:

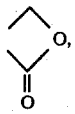

and (A) each of $R^{31}$ and $R^{41}$ is a lower alkoxy and Ring B is a benzene ring of the formula:

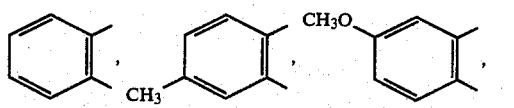

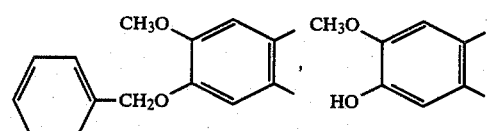

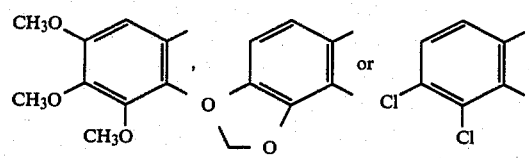

or (B) each of $R^{31}$ and $R^{41}$ is a lower alkoxy of at least 2 carbon atoms, or one of $R^{31}$ and $R^{41}$ is hydrogen atom and the other is methoxy, and Ring B is a benzene ring of the formula:

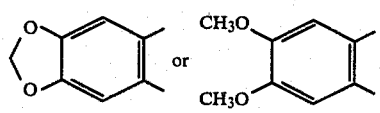

Other preferred examples of the compound (I-a) include those of the formula (I-a) in which each of $R^{11}$ and $R^{21}$ is a lower alkoxycarbonyl, or $R^{11}$ and $R^{21}$ are combined together to form a group of the formula:

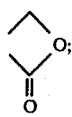

each of $R^{31}$ and $R^{41}$ is a lower alkoxy and Ring B is a benzene ring of the formula:

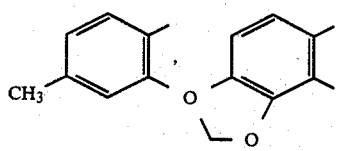

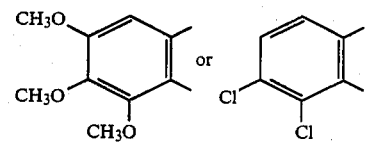

Still other preferred examples include those of the compound (I-a) in which each of $R^{11}$ and $R^{21}$ is a lower alkoxycarbonyl, each of $R^{31}$ and $R^{41}$ is a lower alkoxy and Ring B is a benzene ring of the formula:

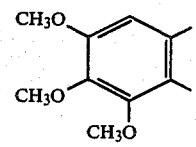

Further preferred examples include those of the compound (I-a) in which each of $R^{11}$ and $R^{21}$ is a lower alkoxycarbonyl or $R^{11}$ and $R^{21}$ are combined together to form a group of the formula:

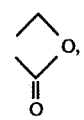

both of $R^{31}$ and $R^{41}$ are methoxy and Ring B is a benzene ring of the formula:

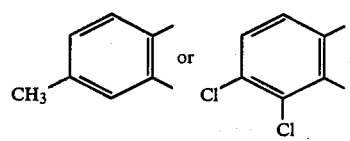

Still further preferred examples include those of the compound (I-a) in which each of $R^{11}$ and $R^{21}$ is a lower alkoxycarbonyl or $R^{11}$ and $R^{21}$ are combined together to form a group of the formula:

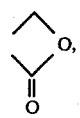

, both of $R^{31}$ and $R^{41}$ are methoxy and Ring B is a benzene ring of the formula:

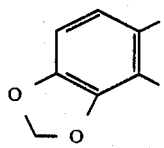

Among the above-mentioned compound (I-a) of the present invention, a compound of the formula:

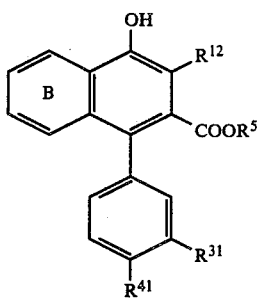
(I-b)

wherein $R^{12}$ is hydrogen atom or a lower alkoxycarbonyl, $R^5$ is a lower alkyl, and $R^{31}$, $R^{41}$ and Ring B are the same as defined above, can be prepared by condensing a compound of the formula:

$$R^{12}-C\equiv C-COOR^5 \quad (II)$$

wherein $R^{12}$ and $R^5$ are the same as defined above, with an aldehyde compound of the formula:

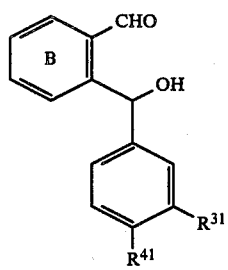
(III)

wherein $R^{31}$, $R^{41}$ and Ring B are the same as defined above, or its di-lower alkyl acetal or a salt thereof.

Alternatively, a compound of the formula:

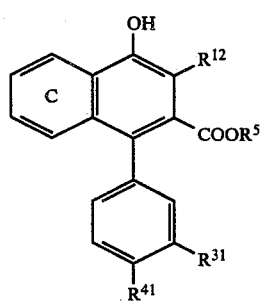
(I-c)

wherein Ring C is a benzene ring of the formula:

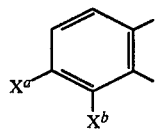

and $R^{12}$, $R^{31}$, $R^{41}$, $R^5$, $X^a$ and $X^b$ are the same as define above, may also be prepared by condensing the compound (II) with a compound of the formula:

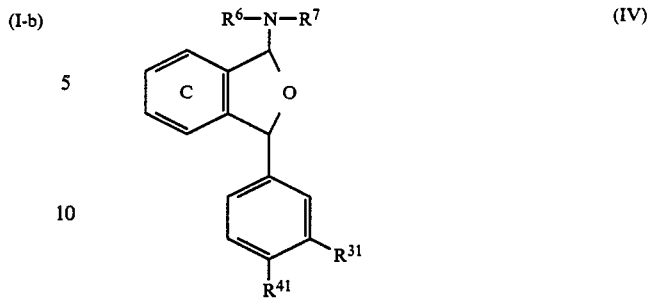
(IV)

wherein $R^6$ is a branched alkyl or a cycloalkyl, $R^7$ is hydrogen atom or a lower alkyl, and $R^{31}$, $R^{41}$ and Ring C are the same as defined above, or a salt thereof.

On the other hand, among the compound (I-a), a compound of the formula:

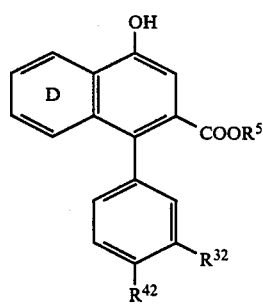
(I-d)

wherein each of $R^{32}$ and $R^{42}$ is a lower alkoxy, or one of $R^{32}$ and $R^{42}$ is hydrogen atom and the other is a lower alkoxy, Ring D is a substituted or unsubstituted benzene ring, and $R^5$ is the same as defined above, with the provisos that if $R^5$ is ethyl and Ring D is a benzene ring of the formula:

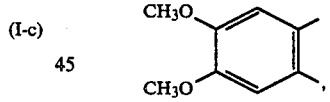

each of $R^{32}$ and $R^{42}$ is a lower alkoxy of at least 2 carbon atoms, or one of $R^{32}$ and $R^{42}$ is hydrogen atom and the other is a lower alkoxy, may be prepared by treating a compound of the formula:

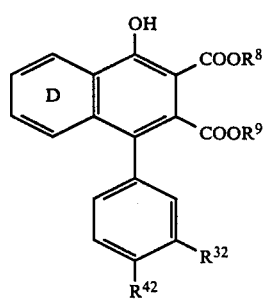
(V)

wherein each of $R^8$ and $R^9$ is a lower alkyl, and $R^{32}$, $R^{42}$ and Ring D are the same as defined above, or a salt thereof, with an alkaline agent to give a compound of the formula:

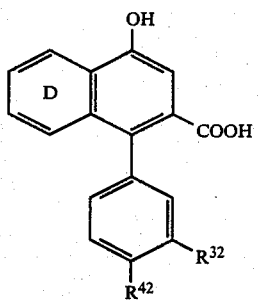

wherein $R^{32}$, $R^{42}$ and Ring D are the same as defined above, followed by esterification thereof.

Moreover, among the compound (I-a), a compound of the formula:

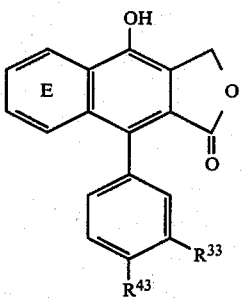

wherein each of $R^{33}$ and $R^{43}$ is a lower alkoxy, or one of $R^{33}$ and $R^{43}$ is hydrogen atom and the other is a lower alkoxy, and Ring E is a substituted or unsubstituted benzene ring with the provisos that if Ring E is a benzene ring of the formula:

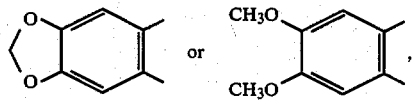

each of $R^{33}$ and $R^{43}$ is a lower alkoxy of at least 2 carbon atoms or one of $R^{33}$ and $R^{43}$ is hydrogen atom and the other is a lower alkoxy, is prepared by reductive lactonization of a compound of the formula:

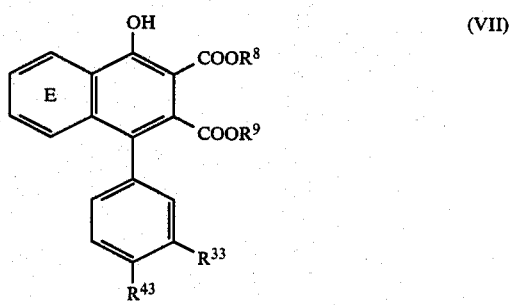

wherein $R^{33}$, $R^{43}$, $R^8$, $R^9$ and Ring E are the same as defined above, or a salt thereof.

The condensation reaction of the compound (II) with the aldehyde compound (III) or its di-lower alkyl acetal or a salt thereof and the condensation reaction of the compound (II) with the compound (IV) or a salt thereof may be accomplished in the presence of an acid in or without a solvent. Examples of the di-lower alkyl acetal of the compound (III) include dimethyl acetal, diethyl acetal, dipropyl acetal, dibutyl acetal and the like. On the other hand, examples of the compound (IV) include those of the formula (IV) in which $R^6$ is cyclopentyl, cyclohexyl, cycloheptyl, isopropyl, sec-butyl or tert-butyl and $R^7$ is hydrogen atom, methyl, ethyl, propyl or butyl. The salt of the aldehyde compound (III) or its di-lower alkyl acetal includes alkali metal salts (e.g., potassium salt, sodium salt) and alkaline earth metal salts (e.g., calcium salts). On the other hand, the salt of the compound (IV) includes inorganic acid addition salts (e.g., hydrochloride) and organic acid addition salts (e.g., p-toluenesulfonate, methanesulfonate). The acid which is used in this reaction includes, for example, inorganic acids such as hydrochloride acid or sulfuric acid; and organic acids such as formic acid, acetic acid, p-toluenesulfonic acid or methanesulfonic acid. Benzene, toluene, xylene or dimethylformamide is suitable as the solvent. It is preferred to carry out the reaction at a temperature between 0° and 150° C., especially at 50° to 100° C.

The aldehyde compound (III) to be used in the above-mentioned reaction is in equilibrium with the compound (III') as shown in the following scheme.

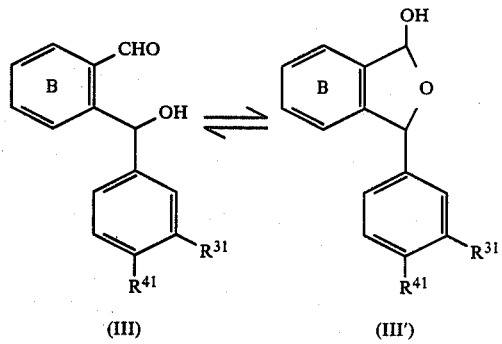

wherein $R^{31}$, $R^{41}$ and Ring B are the same as defined above. Therefore, the compound (III) encompasses within the scope thereof the compound (III') and a mixture of the compounds (III) and (III').

Concomitantly, when in the thus-obtained product (I-b) or (I-c) the lower alkoxycarbonyl group shown by $R^{12}$ is identical with the lower alkoxycarbonyl group shown by the group: —COOR$^5$, said product may be, if required, converted into the compound (I-b) or (I-c) in which said lower alkoxycarbonyl groups are different from each other by reacting the former compound with a lower alkanol of the formula: $R^{1a}$—OH (wherein $R^{1a}$ is a lower alkyl other than $R^5$). Examples of the lower alkanol include methanol, ethanol, propanol and butanol. It is preferred to carry out the reaction in the presence of an alkali metal such as sodium or potassium. It is also preferred to carry it out at a temperature between 0° C. and a refluxing temperature.

The conversion of the compound (V) or a salt thereof (e.g., alkali metal salts, alkaline earth metal salts, quarternary ammonium salts) into the compound (VI) may be accomplished by treating the compound (V) or a salt thereof with an alkali agent in a solvent. Examples of the compound (V) include those of the formula (V) in which each of $R^8$ and $R^9$ is methyl, ethyl, propyl or butyl. The alkali agent which is used in the reaction includes, for example, inorganic bases such as potassium hydroxide or sodium hydroxide. Aqueous alkanols such as aqueous methanol, aqueous ethanol, aqueous propanol or aqueous butanol are suitable as the solvent. It is preferred to carry out the reaction at a temperature between 0° C. and a refluxing temperature.

The subsequent esterification of the thus-obtained compound (VI) may be accomplished by reacting said compound with a lower alkanol. Examples of the lower alkanol include methanol, ethanol, propanol and butanol. When an excess amount of the lower alkanol is used, it is not always necessary to use a solvent because said lower alkanol serves as the solvent. A mixture of the above-mentioned lower alkanol and dioxane may also be used as the solvent. It is preferred to carry out the reaction in the presence of thionyl chloride or hydrogen chloride. It is also preferred to carry it out at a temperature between −10° and 80° C., especially at 0° to 40° C.

The reductive lactonization of the compound (VII) or a salt thereof (e.g., alkali metal salts, alkaline earth metal salts, quarternary ammonium salts) may be accomplished by a conventional method, for example, by treating said compound with a reducing agent in a solvent (e.g., tetrahydrofuran, ethyl ether, dimethoxyethane) at a temperature between 0° C. and a refluxing temperature and then treating the product with a catalytic amount of acid. The reducing agent includes, for example, borane-complexes (e.g., borane-methylsulfide complex, borane-tetrahydrofuran complex, borane-pyridine complex), sodium borohydride-boron trifluoride etherate complex, calcium borohydride, lithium borohydride and lithium aluminum hydride. On the other hand, the acid includes, for example, inorganic acids such as hydrochloric acid and sulfuric acid; and organic acids such as formic acid, acetic acid and methanesulfonic acid.

Concomitantly, when the thus-obtained product (I-b), (I-d) or (I-e) has at least one phenyl-lower alkoxy on Ring B, D or E thereof, said phenyl-lower alkoxy may be, if required, converted into hydroxy by catalytic hydrogenation. Said catalytic hydrogenation may be carried out in the presence of a catalyst (e.g., palladium-charcoal) at 10° to 50° C. in hydrogen atmosphere.

The naphthalene compound (I) of the present invention other than those of the formula (I-a) may be prepared according to either one of the methods described in Journal of the Chemical Society (Chemical Communications), page 354 (1980) and Chemical Abstracts, vol. 53, 20025i (1959) or the methods used for preparation of the compound (I-a).

A pharmaceutically acceptable salt of the naphthalene derivative (I) of the present invention may be readily obtained. For example, such salt may be prepared by treating the naphthalene derivative (I) with an alkali agent such as alkali metal hydroxide (e.g., sodium hydroxide, potassium hydroxide), an alkaline earth metal hydroxide (e.g., calcium hydroxide), a quarternary ammonium hydroxide (e.g., tetramethylammonium hydroxide, tetraethylammonium hydroxide) and the like in a solvent.

Among the starting compounds mentioned above, the di-lower alkyl acetal of the compound (III) may be prepared, for example, by reacting an aldehyde compound of the formula:

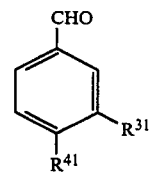

(VIII)

wherein $R^{31}$ and $R^{41}$ are the same as defined above, with an acetal compound of the formula:

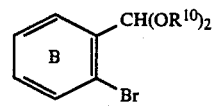

(IX)

wherein $R^{10}$ is a lower alkyl and Ring B is the same as defined above. The thus-obtained di-lower alkyl acetal of the compound (III) may be, if required, converted into the aldehyde compound (III) by treating the former compound with an acid.

Alternatively, the aldehyde compound (III) in which Ring B is a benzene ring of the formula:

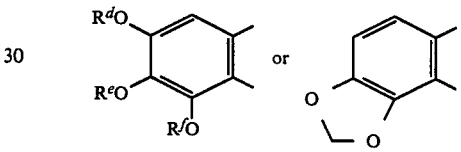

wherein $R^d$, $R^e$ and $R^f$ are the same as defined above, may be prepared, for example, by reacting the compound (VIII) with a compound of the formula:

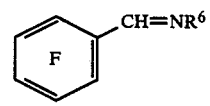

(X)

wherein Ring F is a benzene ring of the formula:

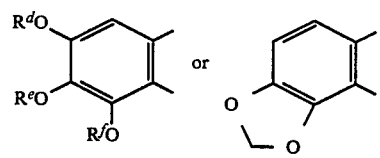

and $R^6$, $R^d$, $R^e$ and $R^f$ are the same as defined above.

Moreoever, the starting compound (IV) may be prepared, for example, by reacting the compound (VIII) with a compound of the formula:

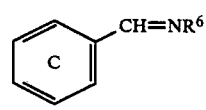

(XI)

wherein $R^6$ and Ring C are the same as defined above, and if required, further reacting the resultant product of the formula:

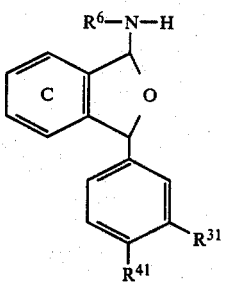

wherein $R^{31}$, $R^{41}$, $R^6$ and Ring C are the same as defined above, with a lower alkyl halide.

The reaction of the compound (VIII) with the compound (IX), (X) or (XI) may be carried out in the presence of an alkyl lithium in a solvent at a temperature between $-100°$ C. and a refluxing temperature. The conversion of the di-lower alkyl acetal of the compound (III) into the free aldehyde compound (III) may be carried out by treating said di-lower alkyl acetal with an acid (e.g., hydrochloric acid, trifluoroacetic acid) in a solvent (e.g., aqueous methanol, aqueous ethanol) at 0° to 30° C. Further, the reaction of the compound (XII) with the lower alkyl halide may be carried out in the presence of an acid acceptor in a solvent at a temperature between $-10°$ and 100° C.

Practical and presently-preferred embodiments of the present invention are illustratively shown in the following Experiments and Examples.

Throughout the Specification and claims, the terms "lower alkyl", "lower alkoxy", "lower alkoxycarbonyl" and "lower alkylenedioxy" should be interpreted as referring to alkyl of one to 4 carbon atoms, alkoxy of one to 4 carbon atoms, alkoxycarbonyl of 2 to 5 carbon atoms and alkylenedioxy of one or 2 carbon atoms, respectively. Further, when $R^1$ (or $R^{11}$) and $R^2$ (or $R^{21}$) are combined together to form a group of the formula:

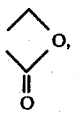

it should be interpreted that said $R^1$ (or $R^{11}$) and $R^2$ (or $R^{21}$) taken together with adjacent naphthol ring form 9-hydroxynaphtho[2,3-c]-furan-3(1H)-one ring of the formula:

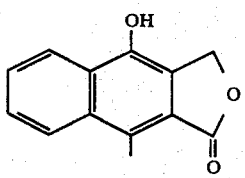

Experiment
(Effect on serum total cholesterol level and serum HDL-cholesterol level)

Male SD rats (body weight: 110 to 170 g, one group consisting of 5 rats) were fed ad libitum for 4 days with a diet containing 2 w/w% of cholesterol and 0.5 w/w% of sodium cholate. Then, the rats were further fed ad libitum with the same diet containing 100 mg% or 20 mg% of a test compound. On the other hand, control group of rats were further fed with the diet not containing the test compound. Three days later, the rats were anesthetized with ether. After the body weight of the rats were measured, blood was collected from abdominal aorta thereof. The blood was allowed to stand at room temperature for one hour and centrifuged. Then, the total cholesterol level in the serum thus obtained was measured enzymatically according to the method described in Clinical Chemistry, vol. 20, page 470 (1974). On the other hand, serum HDL-cholesterol was separated from other forms of cholesterol by the lipoprotein sedimentation method using dextran sulfate [Canadian Journal of Biochemistry, vol. 47, page 1043 (1969)], and then measured enzymatically according to the above-described method. On the basis of the results obtained above, the effects of the test compound on the serum total cholesterol level and on serum HDL-cholesterol level were estimated according to the following formulae:

(Percentage decrease in serum total cholesterol level) =

$$\left[1 - \frac{\text{Average value of serum total cholesterol level in the medicated group}}{\text{Average value of serum total choresterol level in the control group}}\right] \times 100$$

(Percentage increase in serum HDL-cholesterol level) =

$$\left[\frac{\text{Average value of serum HDL-cholesterol level in the medicated group}}{\text{Average value of serum HDL-choresterol level in the control group}} - 1\right] \times 100$$

Note;
*average value of serum total cholesterol level in the control group was 152–230 mg/dl
**average value of seum HDL-cholesterol level in the control group was 13.6–27.6 mg/dl Results are shown in Table 1 and Table 2 below.

TABLE 1

| Test compounds (Amount in the diet: 20 mg %) | Decrease (%) in serum total cholesterol level | Increase (%) in serum HDL-cholesterol level |
|---|---|---|
| 1-(3,4-dimethoxyphenyl)-2,3-bis(methoxycarbonyl)-4-hydroxy-6,7,8-trimethoxynaphthalene | 52 | 86 |
| 1-(3,4-dimethoxyphenyl)-2,3-bis(methoxycarbonyl)-4-hydroxy-7,8-methylenedioxynaphthalene | 52 | 23 |
| 1-(3,4-dimethoxyphenyl)-2,3-bis(methoxycarbonyl)-4-hydroxy-6,7-methylenedioxynaphthalene | 62 | 80 |
| 1-(3,4-dimethoxyphenyl)-3-hydroxymethyl-4-hydroxy-6,7-methylenedioxy-2-naphthoic acid lactone | 51 | 60 |

TABLE 2

| Test compounds (Amount in the diet: 100 mg %) | Decrease (%) in serum total cholesterol level | Increase (%) in serum HDL-cholesterol level |
|---|---|---|
| 1-(3,4-dimethoxyphenyl)-3-hydroxymethyl-4-hydroxy-7-methyl-2-naphthoic acid lactone | 63 | 113 |
| 1-(3,4-dimethoxyphenyl)-2,3-bis(methoxycarbonyl)-4-hydroxy-7-methylnaphthalene | 48 | 76 |
| 1-(3,4-dimethoxyphenyl)-2,3-bis(ethoxycarbonyl)-4-hydroxy-6,7,8-trimethoxynaphthalene | 57 | 93 |
| 1-(3,4-dimethoxyphenyl)-2-methoxycarbonyl-3-ethoxycarbonyl-4-hydroxy-6,7,8-trimethoxynaphthalene | 71 | 178 |
| 1-(3,4-dimethoxyphenyl)-2-ethoxycarbonyl-3-methoxycarbonyl-4-hydroxy-6,7,8-trimethoxynaphthalene | 68 | 144 |
| 1-(3,4-diethoxyphenyl)-2-methoxycarbonyl-4-hydroxy-6,7-methylenedioxynaphthalene | 49 | 44 |
| 1-(3,4-diethoxyphenyl)-3-hydroxymethyl-4-hyroxy-6,7-methylenedioxy-2-naphthoic acid lactone | 60 | 91 |
| 1-(3,4-dimethyoxyphenyl)-2,3-bis(methoxycarbonyl)-4-hydroxy-6-methoxy-7-benzyloxynaphthalene | 45 | 57 |
| 1-(3,4-dimethoxyphenyl)-3-hydroxymethyl-4-hydroxy-6-methoxy-2-naphthoic acid lactone | 37 | 39 |
| 1-(3,4-diethoxyphenyl)-2,3-bis(methoxycarbonyl)-4-hydroxy-6,7-methylenedioxynaphthalene | 60 | 67 |
| 1-(3,4-dimethoxyphenyl)-3-hydroxymethyl-4-hydroxy-2-naphthoic acid lactone | 32 | 36 |

Further, immediately after the collection of blood in the above-mentioned experiment, the liver of each rat was taken out, and the weight thereof was measured. Then, the relative liver weight was examined according to the following formula, and the average relative liver weight was compared with that in the control group. The test compounds used in the above-mentioned experiments caused no substantial increase in the relative liver weight.

(Relative liver weight) = $\frac{\text{Liver weight}}{\text{Body weight}} \times 100$

EXAMPLE 1

(1) A solution of 1.55M n-butyl lithium in 430 ml of hexane is added dropwise to a solution of 204.0 g of 2-bromo-3,4,5-trimethoxybenzaldehyde dimethylacetal in 800 ml of tetrahydrofuran. Said addition is carried out at −70 to −50° C. under stirring for about 15 minutes. The mixture is stirred at −70° to −60° C. for 15 minutes. Then, a solution of 105.5 g of 3,4-dimethoxybenzaldehyde in 300 ml of tetrahydrofuran is added to said mixture at −70° to −50° C. for 15 minutes. The mixture is stirred at the same temperature for 15 minutes and then poured into 2 liters of water. 4 liters of ethyl acetate are added to the aqueous mixture. After shaking, the organic layer is separated from the mixture, washed with water, dried and filtered to remove inorganic materials. Then, the organic layer is evaporated under reduced pressure to remove the solvent, whereby 266 g of 2-(3,4-dimethoxy-α-hydroxybenzyl)-3,4,5-trimethoxybenzaldehyde dimethylacetal are obtained as yellow syrup.

NMR(CDCl$_3$) δ: 3.25 (s, 6H), 3.80 (s, 6H), 3.89 (s, 3H), 4.05 (d, 1H), 5.35 (s, 1H), 6.20 (d, 1H), 6.6–7.2 (m, 4H).

IR $\nu_{max}^{Nujol}$ (cm$^1$): 3450, 1600.

Mass(m/s): 376(M+—CH$_3$OH).

(2) 266 g of 2-(3,4-dimethoxy-α-hydroxybenzyl)-3,4,5-trimethoxybenzaldehyde dimethylacetal are dissolved in 95 ml of benzene. 95 ml of dimethyl acetylenedicarboxylate and 300 mg of p-toluenesulfonic acid·monohydrate are added to the solution. After refluxing for 2 hours, the mixture is cooled and then evaporated under reduced pressure to remove the solvent. 600 ml of methanol are added to the residue, and the mixture is allowed to stand at −30° C. overnight. Crystalline precipitates are collected by filtration and recrystallized from ethyl acetate, whereby 202 g of 1-(3,4-dimethoxyphenyl)-2,3-bis(methoxycarbonyl)-4-hydroxy-6,7,8-trimethoxynaphthalene are obtained as colorless prisms.

m.p. 178°–179° C.

NMR (DMSO-d$_6$) δ: 3.21 (s, 3H), 3.45 (s, 3H), 3.73 (s, 3H), 3.74 (s, 3H), 3.82 (s, 3H), 3.92 (s, 3H), 4.0 (s, 3H), 6.5–7.1 (m, 3H), 7.6 (s, 1H), 11 12.5 (br, 1H).

IR $\nu_{max}^{Nujol}$ (cm$^1$): 1730, 1660, 1595, 1510.

EXAMPLES 2 TO 6

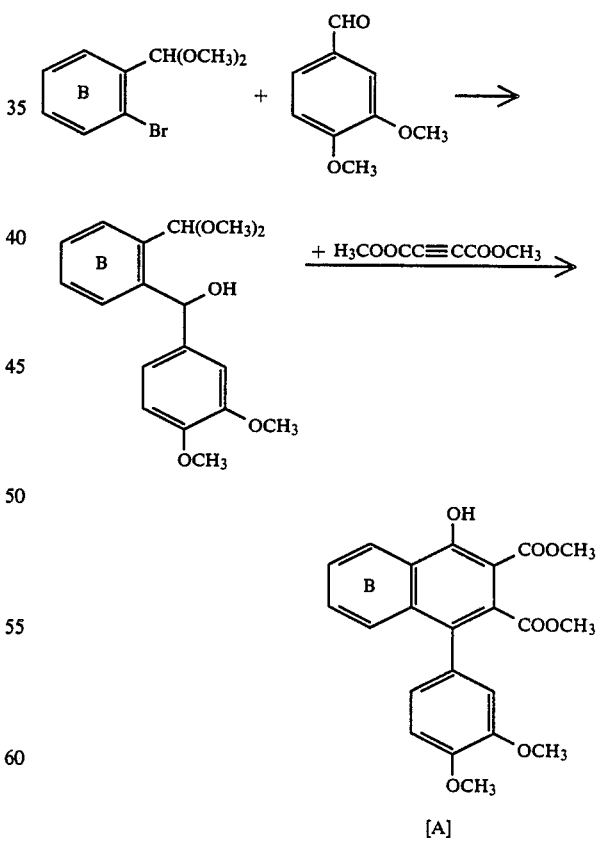

The compounds shown in the following Table 3 are obtained by treating the corresponding starting compounds in the same manner as described in Example 1-(1) and (2).

TABLE 3

| Example Nos. | Compound [A] Ring B | Physical Properties etc.[note] |
|---|---|---|
| 2 | (phenyl, methyl-substituted) | Colorless Crystals, m.p. 182–184° C. IR$\nu_{max}^{Nujol}$ (cm$^{-1}$): 1740, 1660, 1620, 1590, 1520 Mass (m/e): 396 (M$^+$) |
| 3 | CH$_3$-(phenyl)- | Colorless Crystals, m.p. 199–200° C. Mass (m/e): 410 (M$^+$) |
| 4 | CH$_3$O-(phenyl)- | Colorless Crystals, m.p. 178–179° C. IR$\nu_{max}^{Nujol}$ (cm$^{-1}$): 1725, 1660, 1595, 1580, 1510 Mass (m/e): 426 (M$^+$) |
| 5 | CH$_3$O, CH$_3$O-(phenyl)- | Yield: 63% Colorless Crystals, m.p. 208–209° C. IR$\nu_{max}^{Nujol}$ (cm$^{-1}$): 1730, 1660, 1620, 1590, 1510 Mass (m/e): 456 (M$^+$) |
| 6 | CH$_3$O, C$_6$H$_5$CH$_2$O-(phenyl)- | Yield: 53% Colorless Crystals, m.p. 172–174° C. IR$\nu_{max}^{Nujol}$ (cm$^{-1}$): 1730, 1660, 1620, 1590, 1510 Mass (m/e): 532 (M$^+$) |

Note: NMR spectrum data of the compounds shown in Table 3 are as follows.

The compound of Example 2 (CDCl$_3$, δ): 3.58 (s, 3H), 3.76 (s, 3H), 3.90 (s, 3H), 3.99 (s, 3H), 6.7–7.2 (m, 3H), 7.4–7.9 (m, 3H), 8.3–8.6 (m, 1H), 11–13 (br, 1H).

The compound of Example 3 (DMSO-d$_6$+CF$_3$COOD, δ): 2.40 (s, 3H), 3.55 (s, 3H), 3.76 (s, 3H), 3.88 (s, 3H), 3.95 (s, 3H), 6.7–7.2 (m, 3H), 7.2–7.6 (m, 3H), 8.35 (d, 1H, J=9 Hz).

The compound of Example 4 (DMSO-d$_6$, δ): 3.55 (s, 3H), 3.75 (s, 3H), 3.85 (s, 3H), 3.95 (s, 6H), 6.7–7.8 (m, 6H).

The compound of Example 5 (DMSO-d$_6$, δ): 3.55 (s, 3H), 3.68 (s, 3H), 3.78 (s, 3H), 3.88 (s, 3H), 3.93 (s, 3H), 3.97 (s, 3H), 6.7–7.0 (m, 3H), 7.10 (d, 1H, J=8 Hz), 7.66 (s, 1H), 10–12 (br, 1H).

The compound of Example 6 (CDCl$_3$, δ): 3.55 (s, 3H), 3.79 (s, 3H), 3.90 (s, 3H), 4.00 (s, 3H), 4.05 (s, 3H), 5.01 (s, 2H), 6.65 (s, 1H), 6.75 (s, 1H), 6.72 (d, 1H, J=8 Hz), 6.90 (d, 1H, J=8 Hz), 7.20 (s, 5H), 7.70 (s, 1H).

EXAMPLE 7 TO 9

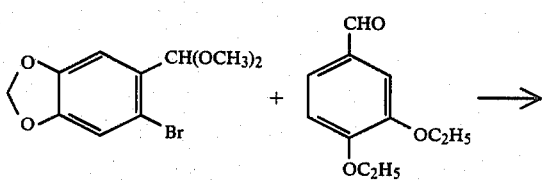

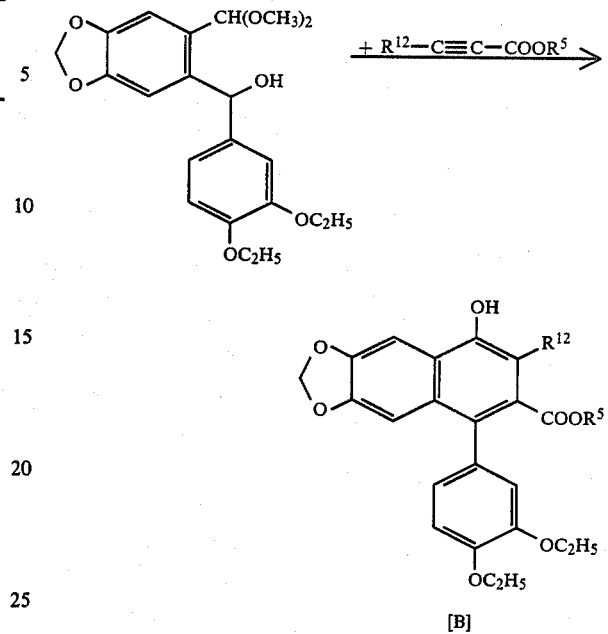

The compounds shown in the following Table 4 are obtained by treating the corresponding starting compounds in the same manner as described in Example 1-(1) and (2).

TABLE 4

| Example Nos. | Compound [B] R$^{12}$/R$^5$ | Physical Properties etc.[note] |
|---|---|---|
| 7 | R$^{12}$ = COOCH$_3$ R$^5$ = CH$_3$ | Yield: 54% Colorless Crystals, m.p. 158–159° C. IR$\nu_{max}^{Nujol}$ (cm$^{-1}$): 1750, 1660, 1620, 1600, 1595 Mass (m/e): 468 (M$^+$) |
| 8 | R$^{12}$ = COOC$_2$H$_5$ R$^5$ = C$_2$H$_5$ | Yield: 59% Colorless Crystals, m.p. 150–151° C. IR$\nu_{max}^{Nujol}$ (cm$^{-1}$): 1740, 1640, 1620, 1600, 1580, 1520, 1500 Mass (m/e): 496 (M$^+$) |
| 9 | R$^{12}$ = H R$^5$ = C$_2$H$_5$ | Yield: 54% m.p. 169–171° C. IR$\nu_{max}^{Nujol}$ (cm$^{-1}$): 3400, 1670, 1625, 1580, 1540, 1515 Mass (m/e): 424 (M$^+$) |

Note: NMR spectrum data of the compounds shown in Table 4 are as follows.

The compound of Example 7 (CDCl$_3$, δ): 1.40 (t, 3H), 1.48 (t, 3H), 3.50 (s, 3H), 3.91 (s, 3H), 4.10 (q, 2H), 4.15 (q, 2H), 6.00 (s, 2H), 6.72 (s, 1H), 6.78 (d, 1H, J=9 Hz), 6.80 (s, 1H), 6.95 (d, 1H, J=9 Hz), 7.70 (s, 1H), 12.12 (s, 1H).

The compound of Example 8 (CDCl$_3$, δ): 1.01 (t, 3H), 1.38 (t, 3H), 1.45 (t, 3H), 1.50 (t, 3H), 4.02 (q, 2H), 4.10 (q, 2H), 4.20 (q, 2H), 4.40 (q, 2H), 6.04 (s, 2H), 6.79 (s, 1H), 6.82 (d, 1H, J=9 Hz), 6.85 (s, 1H), 6.97 (d, 1H), 7.72 (s, 1H), 12.32 (s, 1H).

The compound of Example 9 (CDCl$_3$, δ): 0.93 (t, 3H), 1.41 (t, 3H), 1.50 (t, 3H), 3.9–4.4 (m, 6H), 6.00 (s, 2H), 6.7–7.3 (m, 4H), 7.38 (s, 1H), 7.6 (s, 1H).

EXAMPLE 10

2-Bromo-3,4,5-trimethoxybenzaldehyde dimethylacetal, 3,4-dimethoxybenzaldehyde and diethyl acetylenedicarboxylate are treated in the same manner as described in Example 1-(1) and (2), whereby 1-(3,4-dimethoxyphenyl-2,3-bis(ethoxycarbonyl)-4-hydroxy-6,7,8-trimethoxynaphthalene is obtained as colorless crystals.

m.p. 138°–140° C.

NMR (CDCl$_3$) δ: 1.05 (t, 3H), 1.40 (t, 3H), 3.31 (s, 3H), 3.90 (s, 3H), 3.95 (s, 3H), 3.95 (q, 2H), 3.97 (s, 3H), 4.10 (s, 3H), 4.45 (q, 2H), 6.90 (s, 3H), 7.72 (s, 1H), 12.59 (s, 1H).

IR $\nu_{max}^{Nujol}$ (cm$^{-1}$): 1735, 1720, 1655, 1590, 1510.

Mass (m/e): 514 (M+).

EXAMPLE 11

2-Bromo-3,4,5-trimethoxybenzaldehyde dimethylacetal, 3,4-diethoxybenzaldehyde and dimethyl acetylenedicarboxylate are treated in the same manner as described in Example 1-(1) and (2), whereby 1-(3,4-diethoxyphenyl)-2,3-bis(methoxycarbonyl)-4-hydroxy-6,7,8-trimethoxynaphthalene is obtained as colorless crystals.

m.p. 138°–140° C.

NMR (CDCl$_3$) δ: 1.05 (t, 3H), 1.40 (t, 3H), 3.31 (s, 3H), 3.90 (s, 3H), 3.95 (s, 3H), 3.97 (s, 3H), 4.10 (s, 3H), 4.15 (q, 2H), 4.20 (q, 2H), 6.7–7.0 (m, 3H), 7.69 (s, 1H), 12.36 (s, 1H).

IR $\nu_{max}^{Nujol}$ (cm$^{-1}$): 1740, 1660, 1590, 1510

Mass (m/e): 514 (M+).

EXAMPLE 12

2-Bromo-4,5-methylenedioxybenzaldehyde dimethylacetal, 4-methoxybenzaldehyde and dimethyl acethylenedicarboxylate are treated in the same manner as described in Example 1-(1) and (2), whereby 1-(4-methoxyphenyl)-2,3-bis(methoxycarbonyl)-4-hydroxy-6,7-methylenedioxynaphthalene is obtained as colorless crystals. Yield: 63% m.p. 169°–171° C.

NMR (CDCl$_3$) δ: 3.55 (s, 3H), 3.88 (s, 3H), 3.95 (s, 3H), 6.03 (s, 2H), 6.72 (s, 1H), 6.9–7.4 (m, 4H), 7.75 (s, 1H), 12.20 (s, 1H).

IR $\nu_{max}^{Nujol}$ (cm$^{-1}$): 1740, 1660, 1610, 1520.

Mass (m/e): 410 (M+).

EXAMPLE 13

(1) A solution of 7 g of 3,4-dihydroxybenzaldehyde in 20 ml of dimethyformamide is added dropwise to a mixture of 4.8 g of 60% sodium hydride in 70 ml of dimethylformamide over a period of 15 minutes under ice-cooling. The mixture is stirred at the same temperature for 15 minutes. Then, 50 g of n-propyl iodide are added thereto. After stirring for 12 hours, the mixture is evaporated to remove the solvent. The residue is extracted with ether and the extract is washed with water, dried, filtered to remove inorganic materials and then evaporated to remove the solvent, whereby 8.5 g of 3,4-dipropoxybenzaldehyde are obtained as pale yellow oil.

b.p. 130°–136° C. (at 0.2 mmHg)

(2) 2-Bromo-3,4,5-trimethoxybenzaldehyde dimethylacetal, 3,4-dipropoxybenzaldehyde and dimethyl acetylenedicarboxylate are treated in the same manner as described in Example 1-(1) and (2), whereby 1-(3,4-dipropoxyphenyl)-2,3-bis(methoxycarbonyl)-4-hydroxy-6,7,8-trimethoxynaphthalene is obtained as colorless needles.

m.p. 132° C.

NMR (CDCl$_3$) δ: 0.99 (t, 3H), 1.05 (t, 3H), 1.6–2.1 (m, 4H), 3.21 (s, 3H), 3.42 (s, 3H), 3.73 (s, 3H), 3.77 (s, 3H), 3.89 (s, 3H), 3.8–4.2 (m, 4H), 6.74 (s, 1H), 6.76 (s, 2H), 7.59 (s, 1H), 12.25 (s, 1H).

IR $\nu_{max}^{Nujol}$ (cm$^{-1}$): 1740, 1660, 1570, 1510.

EXAMPLE 14

(1) A solution of 1.55M n-butyl lithium in 20 ml of hexane is added dropwise to a solution of 9.24 g of N-(3,4-methylenedioxybenzylidene)cyclohexylamine in 100 ml of tetrahydrofuran. Said addition is carried out at −70° to −60° C. under stirring for 15 minutes. After the mixture is stirred at the same temperature for further 15 minutes, a solution of 6.65 g of 3,4-dimethoxybenzaldehyde in 15 ml of tetrahydrofuran is added dropwise to the mixture at the same temperature over a period of 15 minutes. The mixture is further stirred at the same temperature for 15 minutes and then poured into a mixture of 300 ml of water and 300 ml of ethyl ether. The organic layer is separated from the mixture, washed with water, dried and evaporated under reduced pressure to remove the solvent. The yellow syrup thus obtained is subjected to column chromatography on silica gel [solvent; benzene-ethyl ether (4:1) saturated with water], and the eluate is evaporated under reduced pressure to remove the solvent. The resultant colorless crystals are recrystallized from a mixture of ethyl acetate and hexane, whereby 8.7 g 3,4-methylenedioxy-2-(3,4-dimethoxy-α-hydroxybenzyl)benzaldehyde are obtained as colorless needles. Yield: 69% m.p. 129°–130° C.

NMR (CDCl$_3$) δ: 3.55 (d, 0.3H, J=9 Hz), 3.70 (d, 0.4H, J=9 Hz), 5.45 (d, 0.3H, J=10 Hz), 3.85 (s, 3H), 3.86 (s, 3H), 5.90 (close m, 2H), 6.0–7.5 (m, 6.7H), 9.70 (s, 0.3H).

IR $\nu_{max}^{Nujol}$ (cm$^{-1}$): 3410, 3300, 1610, 1600, 1520.

Mass (m/e): 316 (M+).

(2) 6.5 g of 3,4-methylenedioxy-2-(3,4-dimethoxy-α-hydroxybenzyl)benzaldehyde are dissolved in 10.5 ml of benzene under heating. 6.5 ml of dimethyl acetylenedicarboxylate and 3 mg of p-toluenesulfonic acid·monohydrate are added to the solution. The mixture is refluxed for 30 minutes. After cooling to room temperature, 300 ml of methanol are added to the mixture, and the mixture is allowed to stand at −30° C. overnight. Crystalline precipitates are collected by filtration and recrystallized from a mixture of tetrahydrofuran and methanol, whereby 7.5 g of 1-(3,4-dimethoxyphenyl)-2,3-bis(methoxycarbonyl)-4-hydroxy-7,8-methylenedioxynaphthalene are obtained as pale yellow prisms. Yield: 83% m.p. 228°–229° C.

NMR (DMSO-d$_6$) δ: 3.50 (s, 3H), 3.74 (s, 3H), 3.82 (s, 3H), 3.91 (s, 3H), 5.92 (s, 2H), 6.7–7.05 (m, 3H), 7.40 (d, 1H, J=9 Hz), 8.05 (d, 1H, J=9 Hz).

IR $\nu_{max}^{Nujol}$ (cm$^{-1}$): 1730, 1659, 1630, 1590, 1510 (br).

Mass (m/e): 440 (M+).

EXAMPLE 15

(1) 1.75 g of 3,4-dichlorobenzaldehyde and 11.88 g of cyclohexylamine are dissolved in 100 ml of benzene. The mixture is refluxed for 4 hours while removing the resultant water with Dien-Stark dehydrating aparatus. The reaction mixture is evaporated to dryness under reduced pressure, whereby 25 g of N-(3,4-dichlorobenzylidene)cyclohexylamine are obtained as pale yellow syrup. Yield: 98%

NMR (CDCl$_3$) δ: 1.0–2.2 (m, 10H), 3.0–3.4 (m, 1H), 7.15 (s, 1H), 7.2–7.8 (m, 3H).

(2) A solution of 1.55M n-butyl lithium in 27 ml of hexane is added dropwise to a solution of 10.24 g of N-(3,4-dichlorobenzylidene)cyclohexylamine in 100 ml of tetrahydrofuran. Said addition is carried out at −70° C. under stirring for 15 minutes. After the mixture is stirred at −70° to −60° C. for further 9 minutes, a solution of 6.65 g of 3,4-dimethoxybenzaldehyde in 20 ml of tetrahydrofuran is added to said mixture at −70° to −50° C. over a period of 15 minutes. After stirring the mixture at the same temperature for further 15 minutes, said mixture is poured into a mixture of 300 ml of water and 300 ml of ethyl ether. The organic layer is separated from the mixture, washed with water, dried and then evaporated under reduced pressure to remove the solvent. The yellow syrup thus-obtained is subjected to column chromatography on silica gel [solvent; ethyl acetate-hexane (1:2)], whereby 8.6 g of 1-(3,4-dimethoxyphenyl)-3-cyclohexylamino-6,7-dichlorophthalane are obtained as colorless crystals. Yield: 51%
m.p. 68°–69° C.

NMR (CDCl$_3$) δ: 0.8–2.3 (m, 11H), 2.7–3.1 (m, 1H), 3.82 (s, 3H), 3.85 (s, 3H), 5.9–6.4 (m, 2H), 6.6–7.0 (m, 3H), 7.22 (d, 1H, J=6 Hz), 7.45 (d, 1H, J=6 Hz).

IR $\nu_{max}^{Nujol}$ (cm$^{-1}$): 3300, 1595, 1510.

(3) 2.1 g of 1-(3,4-dimethoxyphenyl)-3-cyclohexylamino-6,7-dichlorophthalane are dissolved in 3 ml of hexamethylphosphoryltriamide. 0.38 ml of methyl iodide and 0.76 g of potassium carbonate are added to the solution. The mixture is stirred at room temperature for 12 hours. 50 ml of ethyl acetate are added to the reaction mixture. The mixture is washed with water, and the organic layer is separated from the mixture, dried and evaporated under reduced pressure to remove the solvent, whereby 2.1 g of 1-(3,4-dimethoxyphenyl)-3-(N-methyl-N-cyclohexylamino)-6,7-dichlorophthalane are obtained as yellow oil.

(4-a) 2.0 g of 1-(3,4-dimethoxyphenyl)-3-(N-methyl-N-cyclohexylamino)-6,7-dichlorophthalane are dissolved in a mixture of 2.3 ml of benzene and 2 ml of dimethyl acetylenedicarboxylate. 0.4 ml of methanesulfonic acid is added to the solution. The mixture is refluxed for 2 hours under stirring. After cooling the reaction mixture to room temperature, 100 ml of methanol are added to said mixture. The mixture is allowed to stand at −30° C. for 12 hours. Crystalline precipitates are collected by filtration and recrystallized from ethyl acetate, whereby 1.9 g of 1-(3,4-dimethoxyphenyl)-2,3-bis(methoxycarbonyl)-4-hydroxy-7,8-dichloronaphthalene are obtained as colorless prisms. Yield: 83% [overall yield from 1-(3,4-dimethoxyphenyl)-3-cyclohexylamino-6,7-dichlorophthalane]
m.p. 209°–210° C.

NMR (DMSO-d$_6$) δ: 3.50 (s, 3H), 3.75 (s, 3H), 3.85 (s, 3H), 3.95 (s, 3H), 6.6–7.1 (m, 3H), 7.8 (d, 1H, J=9 Hz), 8.4 (d, 1H, J=9 Hz), 11.98 (s, 1H).

IR $\nu_{max}^{Nujol}$ (cm$^{-1}$): 1730, 1660, 1605, 1580, 1510.

(4-b) 4.42 g of 1-(3,4-dimethoxyphenyl)-3-cyclohexylamino-6,7-dichlorophthalane, 4 ml of benzene, 3 ml of dimethyl acetylenedicarboxylate and 0.96 ml of methanesulfonic acid are treated in the same manner as described in paragraph (4-a), whereby 3.34 g of 1-(3,4-dimethoxyphenyl)-2,3-bis(methoxycarbonyl)-4-hydroxy-7,8-dichloronaphthalene are obtained. Yield: 72%

Physical properties of the product are identical with those of the product obtained in paragraph (4-a).

EXAMPLE 16

(1) 2.34 g of 1-(3,4-diethoxyphenyl)-2,3-bis(methoxycarbonyl)-4-hydroxy-6,7-methylenedioxynaphthalene are dissolved in a solution of 2.8 g of potassium hydroxide in a mixture of 20 ml of water and 10 ml of methanol. The solution is refluxed under stirring for 2 hours. 2.8 g of potassium hydroxide are further added to the solution, and the mixture is refluxed for further 24 hours. The mixture is cooled and then 50 ml of chloroform are added thereto. After shaking, the aqueous layer is separated from the mixture and adjusted to pH 1 with 12N hydrochloric acid. Crystalline precipitates are collected by filtration and washed with water and methanol, whereby 1.8 g of 1-(3,4-diethoxyphenyl)-4-hydroxy-6,7-methylenedioxy-2-naphthoic acid are obtained as colorless crystals. Yield: 96%
m.p. 284° C. (decomp.).

NMR (DMSO-d$_6$) δ: 1.31 (t, 3H), 1.40 (t, 3H), 4.05 (q, 2H), 4.13 (q, 2H), 6.11 (s, 2H), 6.6–7.1 (m, 4H), 7.12 (s, 1H), 7.50 (s, 1H), 10.23 (br m, 1H), 12.3 (br, 1H).

Mass (m/e): 396 (M$^+$).

(2) 1.7 g of 1-(3,4-diethoxyphenyl)-4-hydroxy-6,7-methylenedioxy-2-naphthoic acid are dissolved in a mixture of 150 ml of methanol and 100 ml of dioxane. 10 ml of thionyl chloride are added to the solution at room temperature. The mixture is stirred at room temperature for 12 hours, and then evaporated under reduced pressure to remove the solvent, whereby 1.6 g of 1-(3,4-diethoxyphenyl)-2-methoxycarbonyl-4-hydroxy-6,7-methylenedioxynaphthalene are obtained as colorless crystals. Yield: 91%
m.p. 189°–190° C. (recrystallized from methanol).

NMR (CDCl$_3$) δ: 1.38 (t, 3H), 1.44 (t, 3H), 3.53 (s, 3H), 4.05 (q, 2H), 4.13 (q, 2H), 5.93 (s, 2H), 6.6–7.0 (m, 4H), 7.21 (s, 1H), 7.50 (s, 1H).

EXAMPLE 17

0.7 g of 1-(3,4-dimethoxyphenyl)-2,3-bis(methoxycarbonyl)-4-hydroxy-7-methylnaphthalene obtained in Example 3 is dissolved in 30 ml of tetrahydrofuran. 0.24 ml of borane-methylsulfide complex is added to the solution. The mixture is refluxed for 4 hours. After cooling, the reaction mixture is evaporated to dryness under reduced pressure. The residue is dissolved in 300 ml of methanol containing trifluoroacetic acid. The solution is allowed to stand at room temperature for 12 hours, and crystalline precipitates are collected by filtration, whereby 450 mg of 1-(3,4-dimethoxyphenyl)-3-hydroxymethyl-4-hydroxy-7-methyl-2-naphthoic acid lactone are obtained as colorless needles. Yield: 76%
m.p. 234°–236° C.

NMR (DMSO-d$_6$) δ: 2.4 (s, 3H), 3.75 (s, 3H), 3.89 (s, 3H), 5.40 (s, 2H), 6.7–8.4 (m, 6H), 10.2–10.7 (br, 1H).

IR $\nu_{max}^{Nujol}$ (cm$^{-1}$): 3500, 1730, 1660, 1620, 1590, 1515

Mass (m/e): 350 (M$^+$).

EXAMPLE 18 TO 22

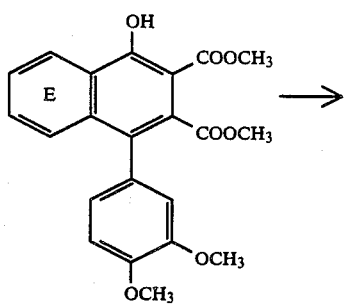

→

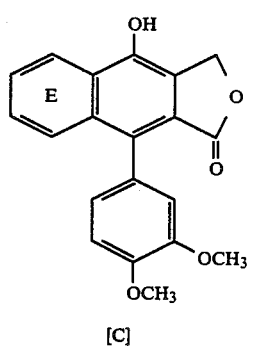

[C]

The compounds shown in the following Table 5 are obtained by treating the corresponding starting compounds in the same manner as described in Example 17.

TABLE 5

| Example Nos. | Compound [C] Ring E | Physical Properties etc.[note] |
|---|---|---|
| 18 | (phenyl) | Yield: 98%<br>Colorless Crystals,<br>m.p. 260° C. (decomp.)<br>IR$\nu_{max}^{Nujol}$ (cm$^{-1}$): 1740, 1630, 1600, 1520<br>Mass (m/e): 336 (M$^+$) |
| 19 | CH$_3$O- (4-methoxyphenyl) | Yield: 92%<br>Colorless Crystals<br>m.p. 254° C. (decomp.)<br>IR$\nu_{max}^{Nujol}$ (cm$^{-1}$): 3200, 1740, 1620, 1580, 1520<br>Mass (m/e): 366 (M$^+$) |
| 20 | CH$_3$O, CH$_3$O, CH$_3$O (trimethoxyphenyl) | Yield: 92%<br>Colorless Crystals<br>m.p. 261° C. (decomp.)<br>IR$\nu_{max}^{Nujol}$ (cm$^{-1}$): 3200, 1740 1720 1620, 1600, 1590, 1540<br>Mass (m/e): 426 (M$^+$) |
| 21 | (methylenedioxyphenyl) | Yield: 91%<br>Yellow Crystals<br>m.p. 273° C. (decomp.)<br>IR$\nu_{max}^{Nujol}$ (cm$^{-1}$): 3420, 1730, 1620, 1590, 1540, 1510<br>Mass (m/e): 380 (M$^+$) |
| 22 | CH$_3$O, C$_6$H$_5$CH$_2$O (methoxy-benzyloxyphenyl) | Yield: 85%<br>Colorless Crystals<br>m.p. 243° C. (decomp.)<br>Mass (m/e): 472 (M$^+$) |

Note: NMR spectrum data of the compounds shown in Table 5 are as follows:

The compound of Example 18 (DMSO-d$_6$, δ): 3.77 (s, 3H), 3.90 (s, 3H), 5.46 (s, 2H), 6.8–7.3 (m, 3H), 7.4–7.9 (m, 3H), 8.3–8.5 (m, 1H).

The compound of Example 19 (DMSO-d$_6$, δ): 3.69 (s, 3H), 3.90 (s, 3H), 4.00 (s, 3H), 5.45 (s, 2H), 6.8–7.3 (m, 4H), 7.6–7.9 (m, 2H)

The compound of Example 20 (DMSO-d$_6$, δ): 3.22 (s, 3H), 3.71 (s, 3H), 3.80 (s, 3H), 3.82 (s, 3H), 4.00 (s, 3H), 5.35 (s, 2H), 6.6–7.1 (m, 3H), 7.55 (s, 1H), 10.45 (s, 1H).

The compound of Example 21 (DMSO-d$_6$, δ): 3.75 (s, 3H), 3.85 (s, 3H), 5.35 (s, 2H), 5.91 (s, 2H), 6.0–7.1 (m, 3H), 7.40 (d, 1H, J=8 Hz), 8.00 (d, 1H, J=8 Hz), 10–11 (br, 1H).

The compound of Example 22 (DMSO-d$_6$, δ): 3.75 (s, 3H), 3.91 (s, 3H), 4.00 (s, 3H), 5.00 (s, 2H), 5.38 (s, 2H), 6.6–7.1 (m, 4H), 7.30 (s, 5H), 7.65 (s, 1H), 10.0–10.6 (br, 1H).

EXAMPLES 23 AND 24

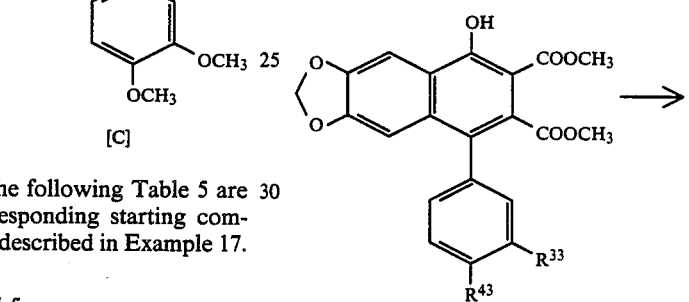

[D]

The compounds shown in the following Table 6 are obtained by treating the corresponding starting compounds in the same manner as described in Example 17.

TABLE 6

| Example Nos. | Compound [D] R$^{33}$/R$^{43}$ | Physical Properties etc.[note] |
|---|---|---|
| 23 | R$^{33}$ = R$^{43}$ = OC$_2$H$_5$ | Yield: 62%<br>Colorless Crystals<br>m.p. 251° C. (decomp.)<br>IR$\nu_{max}^{Nujol}$ (cm$^{-1}$): 3300, 1760, 1630, 1580, 1540, 1520, 1500<br>Mass (m/e): 408 (M$^+$) |
| 24 | R$^{33}$ = H<br>R$^{43}$ = OCH$_3$ | Yield: 87%<br>Colorless Crystals<br>m.p. 297° C. (decomp.)<br>IR$\nu_{max}^{Nujol}$ (cm$^{-1}$): 3150, 1720 1620, 1540, 1520<br>Mass (m/e): 350 (M$^+$) |

Note: NMR spectrum data of the compounds shown in Table 6 are as follows.

The compound of Example 23 (DMSO-$d_6$, δ): 1.31 (t, 3H), 1.40 (t, 3H), 4.05 (q, 2H), 4.10 (q, 2H), 5.35 (s, 2H), 6.15 (s, 2H), 6.89 (s, 1H), 6.6–7.2 (m, 3H), 7.6 (s, 1H), 10.31 (s, 1H).

The Compound of Example 24 (DMSO-$d_6$, δ): 3.89 (s, 3H), 5.39 (s, 2H), 6.18 (s, 2H), 6.85 (s, 1H), 7.0–7.4 (m, 4H), 7.65 (s, 1H).

EXAMPLE 25

1-(3,4-Diethoxyphenyl)-2,3-bis(methoxycarbonyl)-4-hydroxy-6,7,8-trimethoxynaphtalene is treated in the same manner as described in Example 17, whereby 1-(3,4-diethoxyphenyl)-3-hydroxymethyl-4-hydroxy-6,7,8-trimethoxy-2-naphthoic acid lactone is obtained as colorless crystals. Yield: 84% m.p. 219° C. (decomp.).

NMR (DMSO-$d_6$) δ: 1.32 (t, 3H), 1.40 (t, 3H), 3.22 (s, 3H), 3.81 (s, 3H), 4.01 (s, 3H), 4.03 (q, 2H), 4.11 (q, 2H), 5.35 (s, 2H), 6.6–7.0 (m, 3H), 7.56 (s, 1H), 10.40 (br s, 1H).

IR $\nu_{max}^{Nujol}$ (cm$^{-1}$): 3300, 1760, 1605, 1500.

Mass (m/e): 454 (M$^+$).

EXAMPLE 26

1-(3,4-Dimethoxyphenyl)-2,3-bis(methoxycarbonyl)-4-hydroxy-7,8-dichloronaphthalene is treated in the same manner as described in Example 17, whereby 1-(3,4-dimethoxyphenyl)-3-hydroxymethyl-4-hydroxy-7,8-dichloro-2-naphtholic acid lactone is obtained as pale yellow crystals. Yield: 62% m.p. 260° C. (decomp.).

NMR (DMSO-$d_6$) δ: 3.64 (s, 3H), 3.79 (s, 3H), 5.30 (s, 2H), 6.5–7.0 (m, 3H), 7.65 (d, 1H, J=9Hz), 8.25 (d, 1H, J=9Hz), 10.85 (br s, 1H).

IR $\nu_{max}^{Nujol}$ (cm$^{-1}$): 3200, 1725, 1620, 1595, 1510.

EXAMPLE 27

1-(3,4-Dipropoxyphenyl)-2,3-bis(methoxycarbonyl)-4-hydroxy-6,7,8-trimethoxynaphthalene obtained in Example 13 is treated in the same manner as describe in Example 17, whereby 1-(3,4-dipropoxyphenyl)-3-hydroxymethyl-4-hydroxy-6,7,8-trimethoxy-2-naphthoic acid lactone is obtained as colorless crystals.

m.p. 129°–132° C.

NMR (CDCl$_3$+DMSO-$d_6$) δ: 0.99 (t, 3H), 1.04 (t, 3H), 1.6–2.1 (m, 4H), 3.26 (s, 3H), 3.85 (s, 3H), 3.95 (s, 3H), 3.7–4.2 (m, 4H), 5.25 (s, 2H), 6.75 (s, 2H), 6.80 (s, 1H), 7.49 (s, 1H), 9.50 (br s, 1H).

EXAMPLE 28

9.72 g of 1-(3,4-dimethoxyphenyl)-2,3-bis(methoxycarbonyl)-4-hydroxy-6,7,8-trimethoxynaphthalene obtained in Example 1 are added to a sodium ethoxide solution prepared from 500 ml of ethanol and 2.76 g of sodium metal. The mixture is refluxed for 3 hours. The reaction mixture is cooled, and then 7.2 ml of acetic acid are added thereto. The mixture is evaporated to dryness under reduced pressure. The residue is dissolved in 200 ml of chloroform. The chloroform solution is washed with water, dried, filtered to remove inorganic materials and then evaporated to remove the solvent. Crystalline precipitates thus obtained are recrystallized from ethyl acetate, whereby 7.2 g of 1-(3,4-dimethoxyphenyl)-2-methoxycarbonyl-3-ethoxycarbonyl-4-hydroxy-6,7,8-trimethoxynaphthalene are obtained as colorless prisms.

m.p. 151°–152° C.

NMR (CDCl$_3$) δ: 1.31 (t, 3H), 3.22 (s, 3H), 3.41 (s, 3H), 3.80 (s, 3H), 3.87 (s, 3H), 3.90 (s, 3H), 4.00 (s, 3H), 4.35 (q, 2H), 6.76 (s, 3H), 7.60 (s, 1H), 12.42 (s, 1H).

EXAMPLE 29

1-(3,4-dimethoxyphenyl)-2,3-bis(ethoxycarbonyl)-4-hydroxy-6,7,8-trimethoxynaphthalene obtained in Example 10 is treated with a sodium methoxide solution in the same manner as described in Example 28, whereby 1-(3,4-dimethoxyphenyl)-2-ethoxycarbonyl-3-methoxycarbonyl-4-hydroxy-6,7,8-trimethoxynaphthalene is obtained as colorless prisms.

m.p. 157°–159° C.

NMR (CDCl$_3$) δ: 1.03 (t, 3H), 3.22 (s, 3H), 3.8 (s, 3H), 3.75 (s, 3H), 3.87 (s, 6H), 3.9 (q, 2H), 3.98 (s, 3H), 6.77 (s, 3H), 7.59 (s, 1H), 12.29 (s, 1H).

EXAMPLE 30

2-Bromo-4,5-methylenedioxybenzaldehyde dimethylacetal, 3-methoxybenzaldehyde and dimethyl acetylenedicarboxylate are treated in the same manner as described in Example 1, whereby 1-(3-methoxyphenyl)-2,3-bis(methoxycarbonyl)-4-hydroxy-6,7-methylenedioxynaphthalene is obtained.

m.p. 152°–154° C.

IR $\nu_{max}^{Nujol}$ (cm$^{-1}$): 1730, 1660, 1610, 1600.

Mass (m/e): 410 (M$^+$).

NMR (DMSO-$d_6$) δ: 3.5 (s, 3H), 3.80 (s, 3H), 3.90 (s, 3H), 6.15 (s, 2H), 6.60 (s, 1H), 6.7–6.9 (m, 2H), 6.9–7.2 (m, 1H), 7.4 (d, 1H), 7.57 (s, 1H), 11–12 (br, 1H).

EXAMPLE 31

2-Bromo-4,5-methylenedioxybenzaldehyde dimethylacetal, 3,4-diisopropoxybenzaldehyde and diethyl acetylenedicarboxylate are treated in the same manner as described in Example 1, whereby 1-(3,4-diisopropoxyphenyl)-2,3-bis(ethoxycarbonyl)-4-hydroxy-6,7-methylenedioxynaphthalene is obtained. Yield: 51% m.p. 123°–124° C.

Mass (m/e): 524 (M$^+$).

NMR (DMSO-$d_6$) δ: 0.94 (t, 3H), 1.35 (t, 3H), 1.30 (d, 6H), 1.36 (d, 6H), 3.96 (q, 2H), 4.35 (q, 2H), 4.3–4.7 (m, 2H), 6.09 (s, 2H), 6.6–7.1 (m, 4H), 7.55 (s, 1H), 12.19 (s, 1H).

EXAMPLE 32

1-(3-methoxyphenyl)-2,3-bis(methoxycarbonyl)-4-hydroxy-6,7-methylenedioxynaphthalene obtained in Example 30 is treated in the same manner as described in Example 17, whereby 1-(3-methoxyphenyl)-3-hydroxymethyl-4-hydroxy-6,7-methylenedioxy-2-naphthoic acid lactone is obtained. Yield: 90% m.p. 275° C. (decomp.).

IR $\nu_{max}^{Nujol}$ (cm$^{-1}$): 3200, 1740, 1720, 1620, 1600, 1590, 1540.

Mass (m/e): 350 (M$^+$).

NMR (DMSO-$d_6$) δ: 3.80 (s, 3H), 5.40 (s, 2H), 6.15 (s, 2H), 6.80 (s, 1H), 6.8–7.2 (m, 3H), 7.4 (d, 1H), 7.65 (s, 1H), 11.4 (br s, 1H).

EXAMPLE 33

1-(3,4-diisopropoxyphenyl)-2,3-bis(ethoxycarbonyl)-4-hydroxy-6,7-methylenedioxynaphthalene obtained in Example 31 is treated in the same manner as described in Example 17, whereby 1-(3,4-diisopropoxyphenyl)-3-hydroxymethyl-4-hydroxy-6,7-methylenedioxy-2-naphthoic acid lactone is obtained. Yield 82% m.p. 223° C.

NMR (CDCl$_3$) δ: 1.33 (d, 6H), 1.40 (d, 6H), 4.3–4.8 (m, 2H), 5.33 (s, 2H), 6.02 (s, 3H), 6.7–7.1 (m, 4H), 7.64 (s, 1H), 8–10 (br, 1H)

EXAMPLE 34

2 g of 1-(3,4-dimethoxyhenyl)-2,3-bis(methoxycarbonyl)-4-hydroxy-6-methoxy-7-benzyloxynaphthalene obtained in Example 6 are dissolved in a mixture of 200 ml of tetrahydrofuran and 50 ml of methanol. The solution is stirred in the presence of 2 g of 10% palladium-charcoal in hydrogen atmosphere at 40 psi for 2 hours. After the reaction, the catalyst is removed by filtration, and the filtrate is evaporated to dryness under reduced pressure. The resultant crude crystals are triturated with methanol, whereby 1.5 g of 1-(3,4-dimethoxyphenyl)-2,3-bis(methoxycarbonyl)-4-hydroxy-6-methoxy-7-hydroxynaphthalene is obtained.

m.p. 231° C. (decomp.).

IR $\nu_{max}^{Nujol}$ (cm$^{-1}$): 3400, 1730, 1650, 1620, 1600, 1590, 1580, 1510.

NMR (DMSO-d$_6$) δ: 3.5 (s, 3H), 3.74 (s, 3H), 3.82 (s, 3H), 3.90 (s, 3H), 3.95 (s, 3H), 6.6–7.1 (m, 4H), 7.61 (s, 1H), 9.7–10.4 (br, 1H).

EXAMPLE 35

1-(3,4-Dimethoxyphenyl)-3-hydroxymethyl-4-hydroxy-6-methoxy-7-benzyloxy-2-naphthoic acid lactone obtained in Example 22 is treated in the same manner as described in Example 34, whereby 1-(3,4-dimethoxyphenyl)-3-hydroxymethyl-4,7-dihydroxy-6-methoxy-2-naphthoic acid lactone is obtained as colorless microneedles.

m.p. >270° C.

IR $\nu_{max}^{Nujol}$ (cm$^{-1}$): 3420, 1750, 1620, 1600, 1580 (sharp), 1510.

Mass (m/e): 382 (M+).

NMR (DMSO-d$_6$) δ: 3.77 (s, 3H), 3.89 (s, 3H), 3.99 (s, 3H), 5.35 (s, 2H), 6.7–7.3 (m, 4H), 7.6 (s, 1H), 9.0–11.5 (br, 2H).

EXAMPLE 36

2-Bromo-3,4,5-trimethoxybenzaldehyde dimethylacetal, 3-methoxy-4-ethoxybenzaldehyde and dimethyl acetylenedicarboxylate are treated in the same manner as described in Example 1, whereby 1-(3-methoxy-4-ethoxyphenyl)-2,3-bis(methoxycarbonyl)-4-hydroxy-6,7,8-trimethoxynaphthalene is obtained as colorless needles. Yield: 67% m.p. 159° C.

NMR (CDCl$_3$) δ: 1.47 (t, 3H), 3.22 (s, 3H), 3.42 (s, 3H), 3.80 (s, 3H), 3.85 (s, 3H), 3.87 (s, 3H), 4.00 (s, 3H), 4.12 (q, 2H), 6.75 (s, 3H), 7.56 (s, 1H), 12.21 (s, 1H).

IR $\nu_{max}^{Nujol}$ (cm$^{-1}$): 1730, 1710, 1660, 1590, 1510.

EXAMPLE 37

2-Bromo-3,4,5-trimethoxybenzaldehyde dimethylacetal, 3-ethoxy-4-methoxybenzaldehyde and dimethyl acetylenedicarboxylate are treated in the same manner as described in Example 1, whereby 1-(3-ethoxy-4-methoxyphenyl)2,3-bis(methoxycarbonyl)-b 4-hydroxy-6,7,8-trimethoxynaphthalene is obtained as colorless needles. Yield: 65% m.p. 158° C.

NMR (CDCl$_3$) δ: 3.45 (t, 3H), 3.22 (s, 3H), 3.45 (s, 3H), 3.85 (s, 3H), 3.89 (s, 3H), 3.98 (s, 3H), 4.08 (q, 2H), 6.76 (s, 3H), 7.56 (s, 1H), 12.21 (s, 1H).

IR $\nu_{max}^{Nujol}$ (cm$^{-1}$): 1740, 1655, 1590, 1510.

EXAMPLE 38

2-Bromo-4,5-methylenedioxybenzaldehyde dimethylacetal, 3,4-dimethoxybenzaldehyde and dimethyl acetylenedicarboxylate are treated in the same manner as described in Example 1, whereby 1-(3,4-dimethoxyphenyl)-2,3-bis(methoxycarbonyl)-4-hydroxy-6,7-methylenedioxynaphthalene is obtained as colorless crystals.

m.p. 130°–133° C.

IR $\nu_{max}^{Nujol}$ (cm$^{-1}$): 1730, 1672, 1595, 1520.

Mass (m/e): 440 (M+).

NMR (CDCl$_3$) δ: 3.55 (s, 3H), 3.85 (s, 3H), 3.90 (s, 3H), 3.95 (s, 3H), 6.03 (s, 2H), 6.77 (s, 1H), 6.85–6.95 (m, 3H), 7.75 (s, 1H), 12.30 (s, 1H).

EXAMPLE 39

1-(3,4-dimethoxyphenyl)-2,3-bis(methoxycarbonyl)-4-hydroxy-6,7-dimethoxynaphthalene obtained in Example 5 is treated in the same manner as described in Example 17, whereby 1-(3,4-dimethoxyphenyl)-3-hydroxymethyl-4-hydroxy-6,7-dimethoxy-2-naphthoic acid lactone is obtained as colorless crystals. Yield: 82% m.p. 278° C. (decomp.).

IR $\nu_{max}^{Nujol}$ (cm$^{-1}$): 3150, 1740 (sharp), 1700, 1620, 1600, 1580.

Mass (m/e): 396 (M+).

MNR (DMSO-d$_6$) δ: 3.70 (s, 3H), 3.80 (s, 3H), 3.90 (s, 3H), 4.0 (s, 3H), 5.39 (s, 2H), 6.8–7.2 (m, 3H), 7.08 (s, 1H), 7.67 (s, 1H).

EXAMPLE 40

1-(3,4-dimethoxyphenyl)-2,3-bis(methoxycarbonyl)-4-hydroxy-6,7-methylenedioxynaphthalene obtained in Example 38 is treated in the same manner as described in Example 17, whereby 1-(3,4-dimethoxyphenyl)-3-hydroxymethyl-4-hydroxy-6,7-methylenedioxy-4-naphthoic acid lactone is obtained as colorless crystals. Yield: 52% m.p. 256° C. (decomp.).

Physical properties of this compound are identical with those described in Tetrahedron vol. 34, page 1011 (1978).

What we claim is:

1. A naphthalene derivative of the formula:

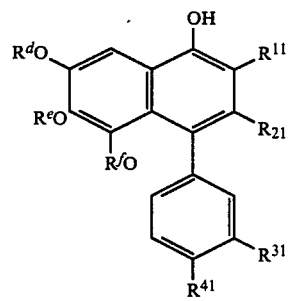

wherein each of $R^{11}$ and $R^{21}$ are a lower alkoxycarbonyl, each of $R^{31}$ and $R^{41}$ is a lower alkoxy, and each of $R^d$, $R^e$ and $R^f$ is a lower alkyl or a pharmaceutically acceptable salt thereof.

2. The compound according to claim 1, which is 1-(3,4-dimethoxyphenyl)-2,3-bis(ethoxycarbonyl)-4-hydroxy-6,7,8-trimethoxynaphthalene or a pharmaceutically acceptable salt thereof.

3. A naphthalene derivative of the formula:

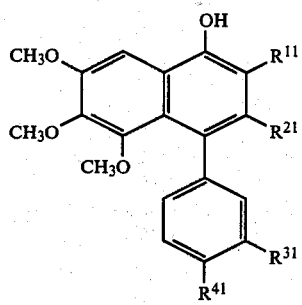

wherein each of $R^{11}$ and $R^{21}$ is a lower alkoxycarbonyl and each of $R^{31}$ and $R^{41}$ is a lower alkoxy, or a pharmaceutically acceptable salt thereof.

4. The compound according to claim 3, in which each of $R^{11}$ and $R^{21}$ is methoxycarbonyl or ethoxycarbonyl and each of $R^{31}$ and $R^{41}$ is methoxy or ethoxy.

5. The compound according to claim 3, which is 1-(3,4-dimethoxyphenyl)-2,3-bis(methoxycarbonyl)-4-hydroxy-6,7,8-trimethoxynaphthalene or a pharmaceutically acceptable salt thereof.

6. A pharmaceutical composition having a hypolipidemic activity comprising a therapeutically effective amount of a naphthalene derivative of claim 1, and a pharmaceutically acceptable carrier.

7. A phramaceutical composition having a hypolipidemic activity comprising a therapeutically effective amount of a naphthalene derivative of claim 3, and a pharmaceutically acceptable carrier.

* * * * *

UNITED STATES PATENT AND TRADEMARK OFFICE
CERTIFICATE OF CORRECTION

PATENT NO. : 4,771,072
DATED : September 13, 1988
INVENTOR(S) : IWASAKI et al.

It is certified that error appears in the above-identified patent and that said Letters Patent is hereby corrected as shown below:

Column 32: Correct the formula in claim 1 to read:

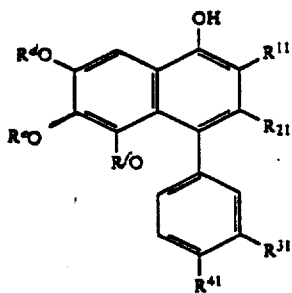

Change the dependency of claim 2 to read --according to claim 3--.

Signed and Sealed this

Fourth Day of April, 1989

Attest:

DONALD J. QUIGG

Attesting Officer

Commissioner of Patents and Trademarks